(12) United States Patent
Mann (10) Patent No.: US 7,491,176 B2
(45) Date of Patent: Feb. 17, 2009

(54) KIT FOR OBTAINING AN ENDOARTERIAL BIOPSY SAMPLE

(75) Inventor: David Marshall Mann, San Diego, CA (US)

(73) Assignee: Vascular BioSciences, San Diego, CA (US)

( * ) Notice: Subject to any disclaimer, the term of this patent is extended or adjusted under 35 U.S.C. 154(b) by 446 days.

(21) Appl. No.: 10/415,719

(22) PCT Filed: Nov. 1, 2001

(86) PCT No.: PCT/IB01/02767

§ 371 (c)(1),
(2), (4) Date: Apr. 30, 2003

(87) PCT Pub. No.: WO02/36017

PCT Pub. Date: May 10, 2002

(65) Prior Publication Data

US 2004/0031721 A1    Feb. 19, 2004

(51) Int. Cl.
| | |
|---|---|
| A61B 10/00 | (2006.01) |
| A61B 17/32 | (2006.01) |
| A61B 17/14 | (2006.01) |
| A61B 17/34 | (2006.01) |
| B65D 83/10 | (2006.01) |
| B65D 1/34 | (2006.01) |
| B65D 6/04 | (2006.01) |
| B65D 69/00 | (2006.01) |
| B65D 71/00 | (2006.01) |

(52) U.S. Cl. .......... 600/564; 600/562; 600/565; 600/566; 600/567; 606/167; 606/170; 606/181; 606/185; 206/363; 206/364; 206/365; 206/366; 206/367; 206/370; 206/577; 206/561; 206/562; 206/563

(58) Field of Classification Search .......... 600/564, 600/562, 565, 566, 567; 606/167, 170, 181, 606/185; 206/363–367, 370, 557, 561–563
See application file for complete search history.

(56) References Cited

U.S. PATENT DOCUMENTS

| | | | | |
|---|---|---|---|---|
| 3,802,555 | A | * | 4/1974 | Grasty et al. ............... 206/572 |
| 4,834,710 | A | * | 5/1989 | Fleck ....................... 604/171 |
| 5,158,543 | A | * | 10/1992 | Lazarus ................... 604/164.1 |
| 5,217,442 | A | * | 6/1993 | Davis ....................... 604/285 |
| 5,287,857 | A | | 2/1994 | Mann |
| 5,392,917 | A | * | 2/1995 | Alpern et al. ............. 206/570 |
| 5,406,959 | A | * | 4/1995 | Mann ........................ 600/566 |
| 5,512,048 | A | * | 4/1996 | Slettenmark ............ 604/288.01 |
| 5,554,097 | A | * | 9/1996 | Guy .......................... 600/102 |
| 5,554,151 | A | | 9/1996 | Hinchliffe |

(Continued)

OTHER PUBLICATIONS

Michelakis, Evangelos D., "Spatio-Temporal Diversity of Apoptosis Within the Vascular Wall in Pulmonary Arterial Hypertension" Circ. Res. 98:172-175 (2006).

Primary Examiner—Max Hindenburg
Assistant Examiner—Jeffrey G Hoekstra
(74) Attorney, Agent, or Firm—Catalyst Law Group APC; David M. Kohn (57) ABSTRACT

A kit for obtaining an endoarterial biopsy sample from a patient including packaging material enclosing one or more kit components; the kit components include instruments use to perform a surgical procedure; and the kit includes separate phase specific packaging parts.

9 Claims, 8 Drawing Sheets

U.S. PATENT DOCUMENTS

| | | | |
|---|---|---|---|
| 5,564,436 A * | 10/1996 | Hakky et al. ................ | 600/567 |
| 5,817,032 A * | 10/1998 | Williamson et al. ......... | 600/562 |
| 5,957,865 A | 9/1999 | Backman et al. | |
| 5,967,781 A * | 10/1999 | Gittleman .................. | 433/172 |
| 6,065,597 A | 5/2000 | Pettersson et al. | |
| 6,231,587 B1 * | 5/2001 | Makower ................... | 606/198 |
| 6,306,132 B1 * | 10/2001 | Moorman et al. ............ | 606/41 |
| 6,468,279 B1 * | 10/2002 | Reo ........................... | 606/79 |

* cited by examiner

KIT FOR OBTAINING AN ENDOARTERIAL BIOPSY SAMPLE

FIELD OF THE INVENTION

The present invention relates to a kit for obtaining an endoarterial biopsy sample from a patient comprising a package and a catheter for harvesting an endoarterial biopsy sample.

BACKGROUND OF THE INVENTION

Cardiovascular catheterization procedures often require a plurality of instruments and equipment to successfully complete the procedure. In view of the number and variety of procedures performed in a modern catheterization facility, there is a need for an improved method of supply all necessary articles to perform any particular type of cardiovascular catheterization in an efficient and organized fashion.

U.S. Pat. Nos. 5,406,959 and 5,287,857, both of which are herein incorporated by reference in their entirety, describe a new variety of catheters which can be used to obtain an endoarterial biopsy sample of one or more interior layers of a patient's selected artery.

It should be noted that U.S. Pat. No. 5,392,917 discloses a surgical instrumentation kit comprising various packaging parts in the form of trays which carry various surgical components. The various packaging parts may be used if necessary and/or may be used alternatively.

In the state of the art, all parts necessary for performing a catheterization procedure are packaged separately. This leads to a number of problems during the catheterization procedure, such as:

- disorderly handling of the various instruments;
- the compatibility of diameters and length is not certain because the operating assistants have to match the various components themselves, which sometimes leads to mistakes;
- sometimes not all necessary instruments are present because the operating assistants forgot to make ready all instruments before starting the operating procedure;
- it takes time for the operating assistants to organize all the necessary parts, in view thereof the preparation of the procedure is costly.

In view of the above, there is a need for a kit comprising those necessary medical supplies and instruments for deployment and use of catheters, such as those described in U.S. Pat. Nos. 5,406,959 and 5,287,857. Such a kit would allow for the speedy set-up and use of an endoarterial biopsy catheter, thereby efficiently using medical resources, and quickly obtaining an endoarterial biopsy sample.

Moreover, once an endoarterial biopsy sample is obtained, there is a need for instruments and materials for the handling, storage and shipment of such samples.

SUMMARY OF THE INVENTION

In order to meet these objects the invention provides a kit for obtaining an endoarterial biopsy sample from a patient in a sequence of phases, the kit comprising a packaging enclosing one or more kit components, wherein the kit components comprise an endoarterial biopsy catheter, the packaging comprising a number of separate packaging parts at least one of which comprises a number of kit components, wherein the kit components which are packaged in a said packaging part are necessary for the same phase of the procedure.

Preferably, the kit comprises:

- a first packaging part containing the percutaneous access components comprising e.g. the percutaneous access needle, an introducer sheath with dilator and guidewire;
- a second packaging part containing components to get access to the desired area of a vasculature and to provide a sterile connection to a vacuum pump, comprising e.g. connective tubing to vacuum pump, a floppy guidewire, an endhole catheter and a stiff guidewire;
- a third packaging part containing e.g. an endoarterial biopsy catheter, a long introducer sheath with dilator and syringes;
- a fourth packaging part containing e.g. various specimen containers, biopsy cassettes and a needle; and
- a fifth packaging part containing e.g. a vacuum pump, vacuum gauges and canisters.

BRIEF DESCRIPTION OF THE DRAWINGS

The foregoing and other objects, features and advantages of the present invention will be apparent from the following description and apparent from the accompanying drawings, in which like reference characters refer to the same parts throughout the different views.

DETAILED DESCRIPTION OF THE INVENTION

The kit for obtaining an endoarterial biopsy sample comprises necessary and accessory medical supplies and/or instrumentation to be used when deploying an endoarterial biopsy catheter.

For purposes of the present invention the term "endoarterial biopsy catheter" refers to any catheter which may be employed to obtain an endoarterial biopsy sample from a living patient, including but not limited to those described in U.S. Pat. Nos. 5,287,857 and 5,406,959.

The skilled artisan will recognize that the term "endoarterial biopsy" refers to a method of obtaining a sample of an artery from the interior of the blood vessel.

The term patient is meant to encompass human beings and mammals. Veterinary utilities including those relating to horses, cows, pigs, sheep, goats, dogs and cats are explicitly within the contemplation of the present invention.

The term "returned mail materials" refers to any of the well-known packaging and postage or courier mechanisms available to transfer one or more sample containers from a health care facility where an endoarterial biopsy catheter can be used, to a remote location such as a diagnostic laboratory or other testing facility, a gene therapy lab, a cell culture facility, or other therapeutic establishment. Return mail materials would specifically include, for example, containers, such as boxes and mail pouches of all types, shapes and sizes. Mailing labels can also be employed in conjunction with the other return mail materials. The skilled artisan will appreciate that all packaging and all postal methods, public and private, fall within the intended scope of the present invention.

The individual components of the kit of the present invention are most easily described as they relate to the established procedure used for obtaining an endoarterial biopsy sample.

Initially the patient is prepared for a cardiac catheterization using methods known in the art, including cleaning all relevant skin surfaces with an appropriate antiseptic and/or application of an appropriate anaesthetic. Typically access to a desired biopsy site can be made via the internal jugular vein or alternately the femoral vein. The desired vein can be accessed percutaneously using a hollow core needle of appropriate size for any given patient.

Any hollow core needle, also known as a percutaneous access needle, which will serve to introduce a guide wire into the patient's vascular system can be used as a component of the present kit.

A short introducer sheath is exchanged for the percutaneous access needle by passing a guidewire of suitable size through the lumen of the needle, and the needle is then removed, leaving the guidewire in the artery.

For purposes of the present invention, any guide wire capable of directing the endoarterial biopsy catheter to its intended location in the patient's vascular system may be made a part of the kit.

A short introducer sheath with dilator is then threaded over the guidewire into the vein. Any suitable introducer sheath and dilator may be used in the present invention.

Figure 1:
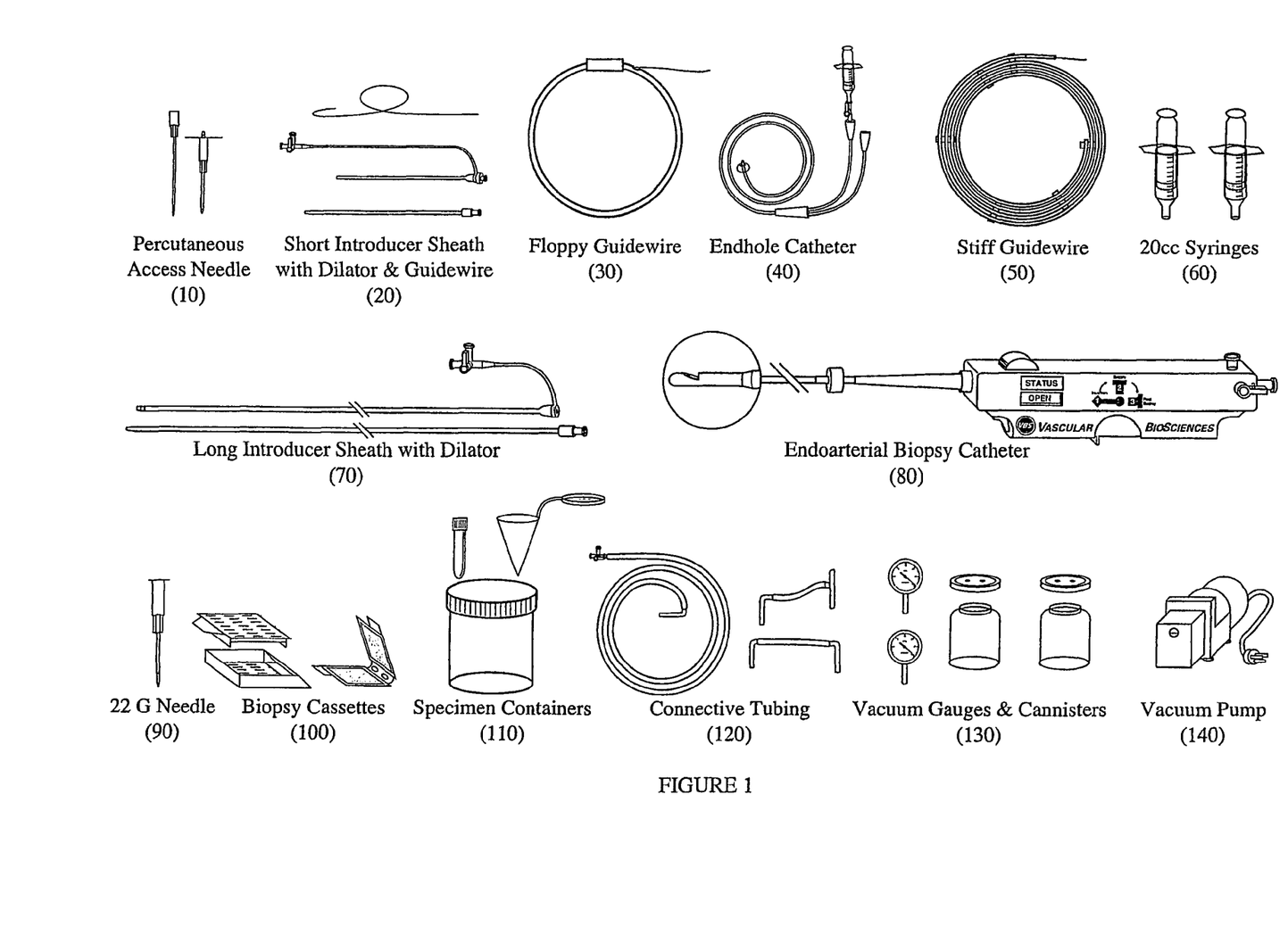
FIG. 1 is representative of the various components, one or more of which can be used in the kit of the present invention including a) an endoarterial biopsy catheter (80); b) percutaneous access needle (10); c) short introducer sheath wit dilator and guidewire (20); d) floppy guidewire (30); e) endhole catheter with inflation syringe (40); f) stiff guidewire (50); g) 20 cc syringes (60); h) long introducer sheath with dilator (70); i) 22 gauge needle for specimen removal (90); j) biopsy cassettes (100); k) specimen containers (11); l) connective tubing (120); m) vacuum gauges and canisters (130); and n) vacuum pump (140)
Figure 2:
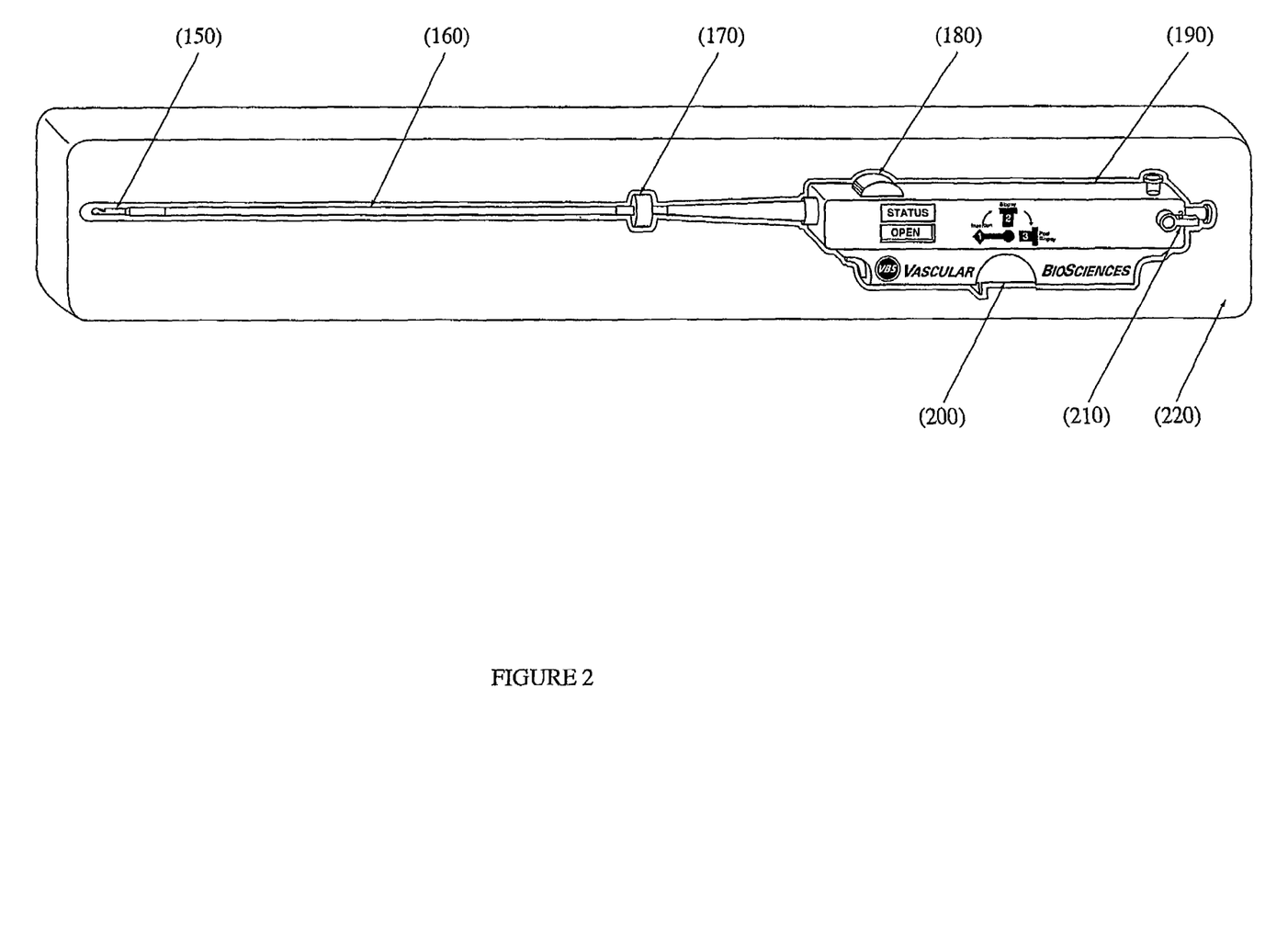
FIG. 2 is a perspective of an "essential endoarterial biopsy catheter kit" showing the cutting tip of the catheter (150), the tubing of the catheter (160), the sheath introducer (170), the trigger (180), the handle body (190), the cocking slide (200), the stopcock (210), and vacuum formed polymer packaging tray (220)
Figure 3:
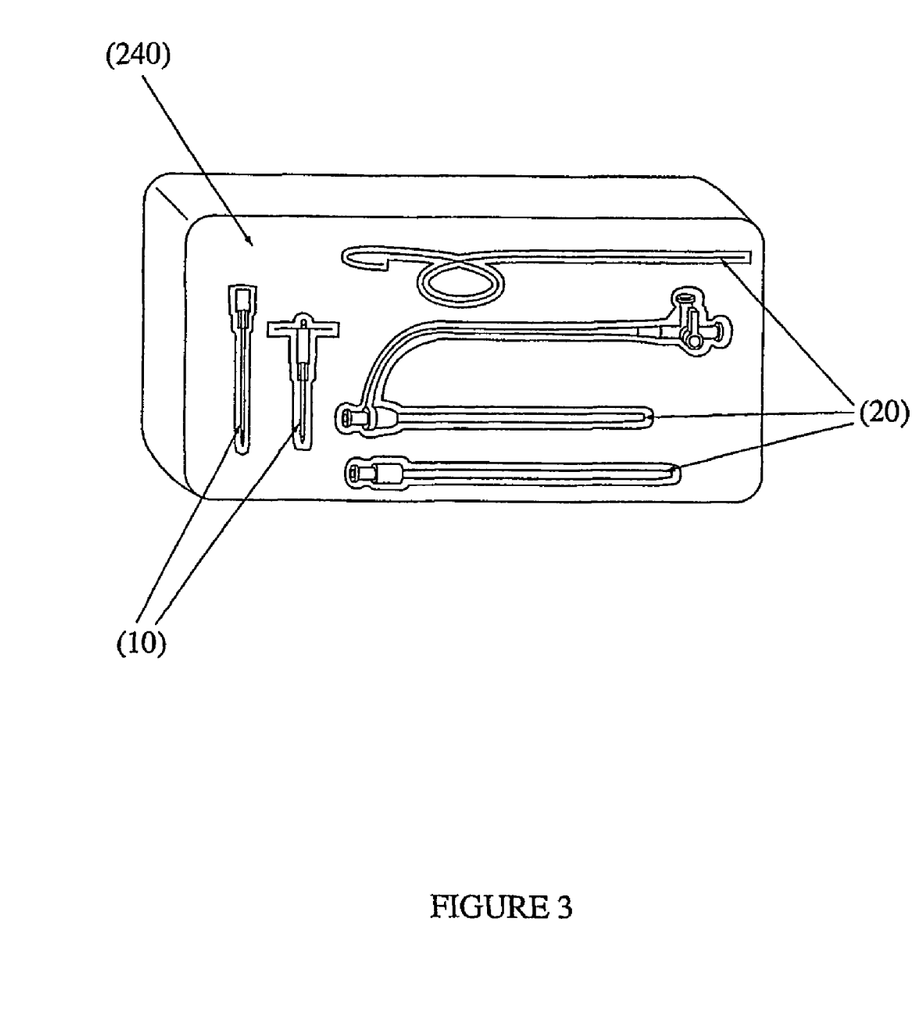
FIG. 3 is a perspective view of a first packaging part containing the percutaneous access components comprising e.g. the percutaneous access needle (10), an introducer sheath with dilator and guidewire (20)
Figure 4:
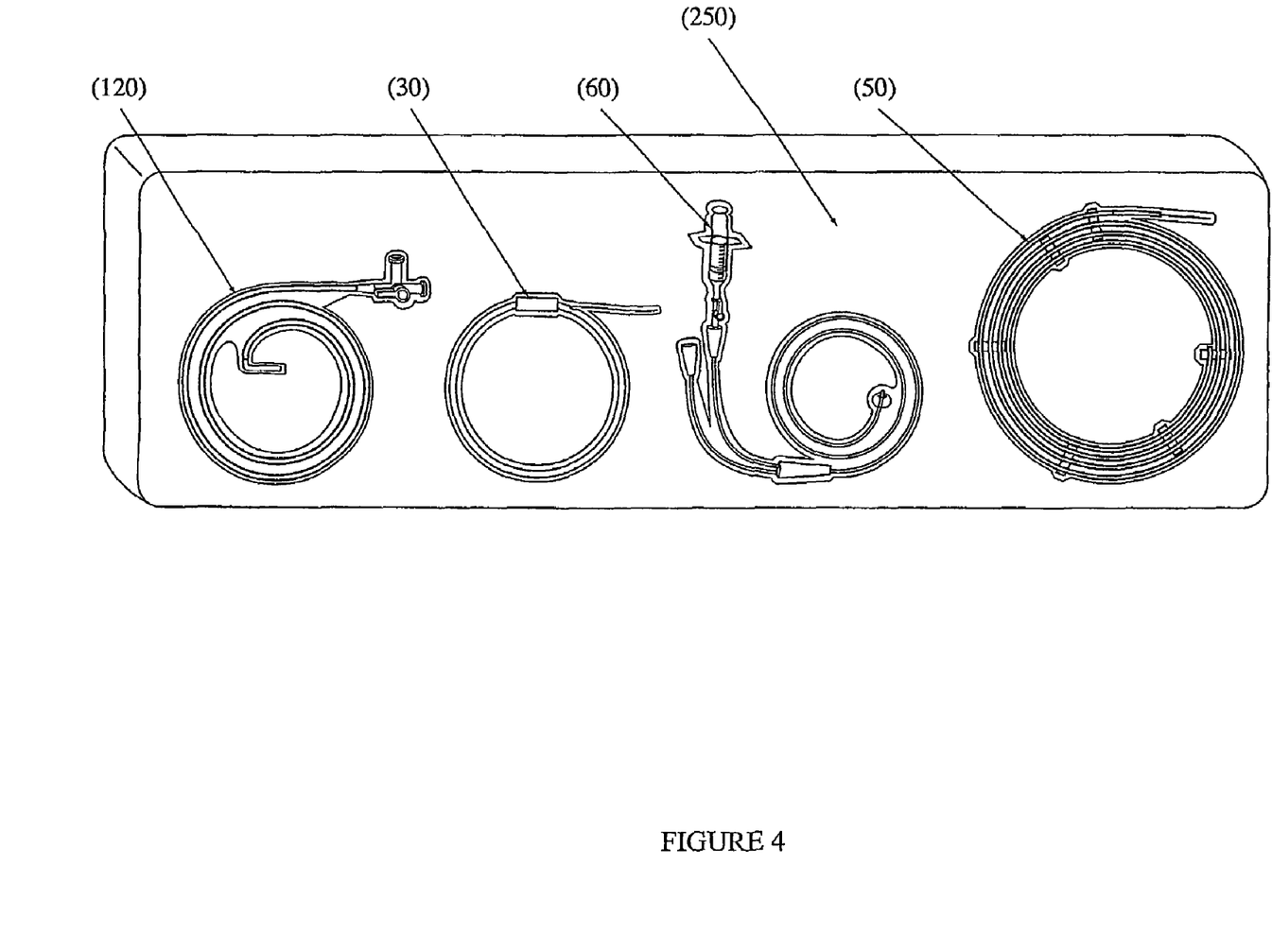
FIG. 4 is a perspective view of a second packaging part containing components to get access to the desired area of a vasculature and to provide a sterile connection to a vacuum pump, comprising e.g. connective tubing to vacuum pump (120), a floppy guidewire (30), an endhole catheter (40) and a stiff guidewire (50)

The guidewire is then removed, followed by the dilator leaving the short introducer sheath allowing homeostatic access to the desired vein. As all these components are currently preferred for use in the first phase of the procedure, they may all be preferably stored in a first packaging part (240) as shown in FIG. 3.

In this example, biopsy specimens are desired from the pulmonary arteries located in the right lung. To access the desired location in the vasculature, an endhole catheter is floated through the right atrium and the right ventricle to a pulmonary artery and then to the desired location in the pulmonary arterial system. More difficult areas of the pulmonary can be reached by passing a floppy guidewire through the endhole catheter, manipulating the floppy guidewire into the desired location, advancing the endhole catheter over the floppy guidewire, removing the floppy guidewire, leaving the endhole catheter in the desired location.

Figure 5:
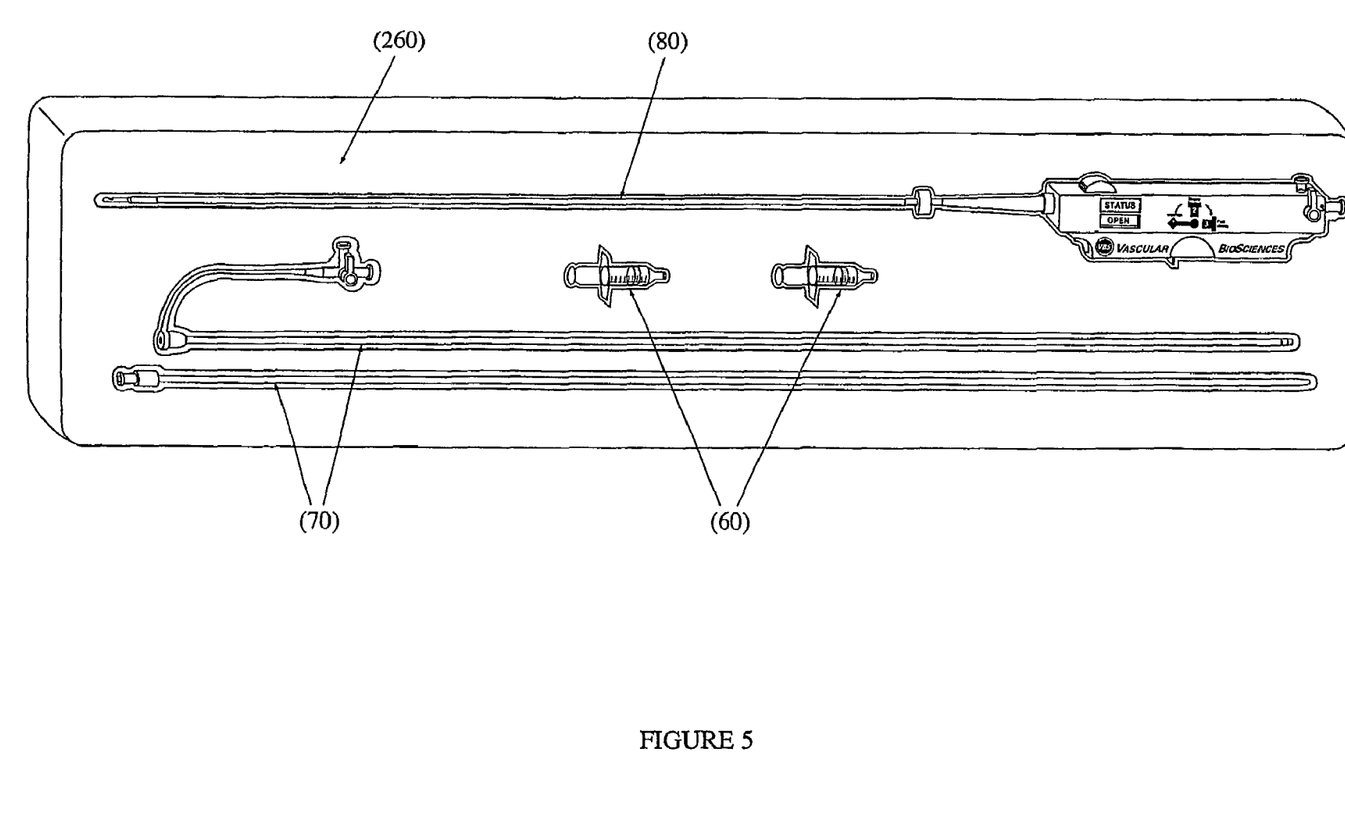
FIG. 5 is a perspective view of a third packaging part containing e.g. an endoarterial biopsy catheter (80), a long introducer sheath with dilator (70) and syringes (60)

A stiff guidewire is then is then passed through the end whole catheter passed through the endhole catheter, and the endhole catheter is removed, leaving the stiff wire in the desired location. As all these components are currently preferred for use in a second phase of the procedure, they may all be preferably stored in a second packaging part (250) as shown in FIG. 5.

Figure 6:
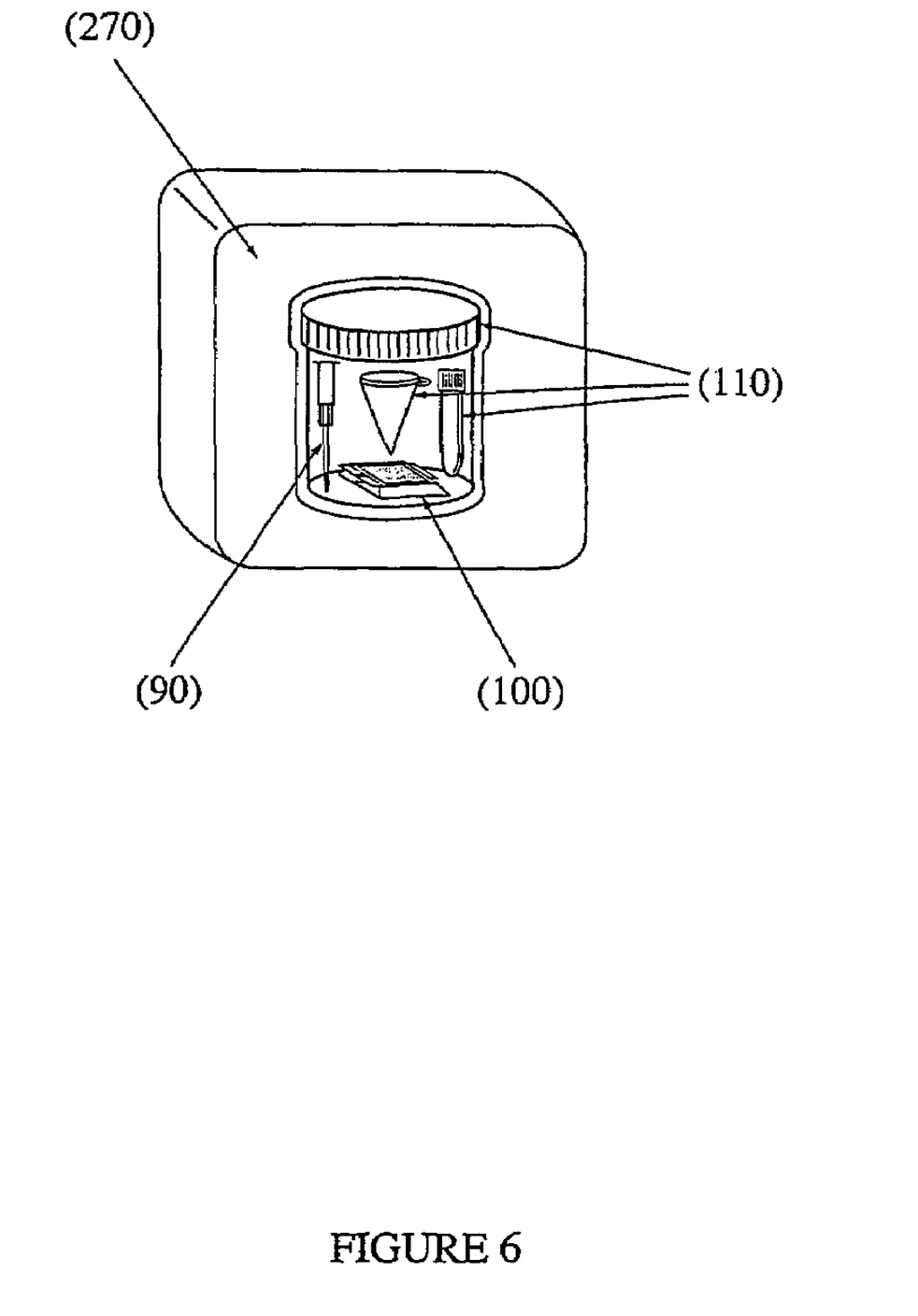
FIG. 6 is a perspective view of a fourth packaging part containing e.g. various specimen containers (110), biopsy cassettes (100) and a needle (90)

Then, a long introducer sheath having a radiopaque marker as it's distal end with dilator is passed over the stiff guidewire, the guidewire and dilator are then removed, leaving the long introducer sheath at the desired location. The endhole catheter then reintroduced to the desired site through the long introducer sheath and an angiogram is performed by injecting contrast solution with simultaneous fluoroscopy. Alternatively, an angiographic catheter can be used instead of an endhole catheter to perform the angiogram. Accordingly an angiographic catheter can also make up one of the components of the present invention. The endhole catheter is then removed and the endoarterial biopsy catheter is introduced to the desired site through the long introducer sheath. As all these components are currently preferred for use in a third phase of the procedure, they may all be preferably stored in a third packaging part (260) as shown in FIG. 6. As set forth above any biopsy catheter may be employed as a component of the present kit, including, but not limited to those described in U.S. Pat. Nos. 5,406,959 and 5,287,857.

The desired relationship between the biopsy catheter and the introducer sheath is achieved when the suction tip and cutting tip of the biopsy catheter clear the open end of the introducer sheath. During this step, the suction tip and cutting tip (i.e., the cutting portion of the biopsy catheter) are aligned in the closed configuration, to enable easier passage through the bends and curves of the introducer sheath. The stopcock on the biopsy catheter is closed to prevent fluid flow during this step.

Upon further fluoroscopic visualization of the biopsy catheter and radiopaque marker on the introducer sheath, the biopsy catheter is positioned to the desired area and the cutting portion of the biopsy catheter is opened. With the suction tip and cutting tip in the open position, the bevelled opening on the suction tip is exposed. The cutting tip is retracted to expose the bevelled opening. Once the desired location is achieved, the vacuum system is evacuated up to the stopcock at the distal end of vacuum tubing.

Once a full vacuum is established (approximately 29.5 in Hg vacuum), according to vacuum gauges, both stopcocks are opened transmitting the vacuum to the bevelled opening of the suction tip. This draws endoarterial tissue from the arterial wall into the bevelled opening of the suction tip. The cutter tip is advanced over the suction tip, severing the endoarterial biopsy sample maintained by vacuum in the cutter tip. The biopsy catheter is then completely removed from the patient and the cutter tip is retracted from the suction tip revealing the biopsy specimen captured within the bevelled opening.

The biopsy sample is removed from the bevelled opening with a suitable instrument, for example a 22 gauge needle. The biopsy sample is placed in a biopsy cassette, or, optionally into a specimen container. As all these components are currently preferred for use in a fourth phase of the procedure, they may all be preferably stored in a fourth packaging part (270). The type and contents of the specimen container making up one component of the present kit may be chosen from a wide array of sample containers depending upon the end use of the endoarterial biopsy sample.

The first to the fourth packaging parts (240-270) all contain disposable parts, which can only be used in one procedure for one patient.

Figure 7:
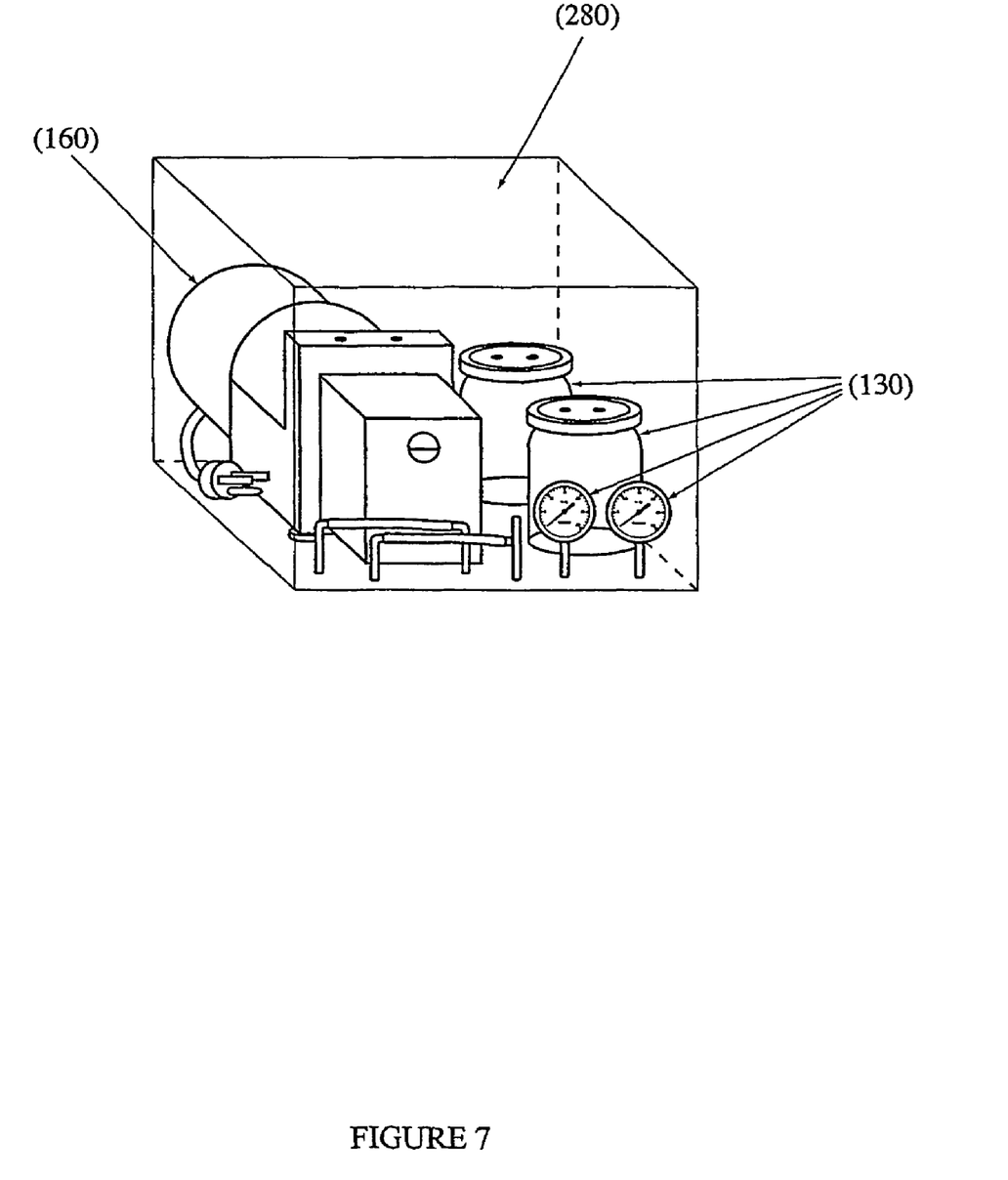
FIG. 7 is a perspective view of a fifth packaging part containing e.g. a vacuum pump (140), vacuum gauges and canisters (130)
Figure 8:
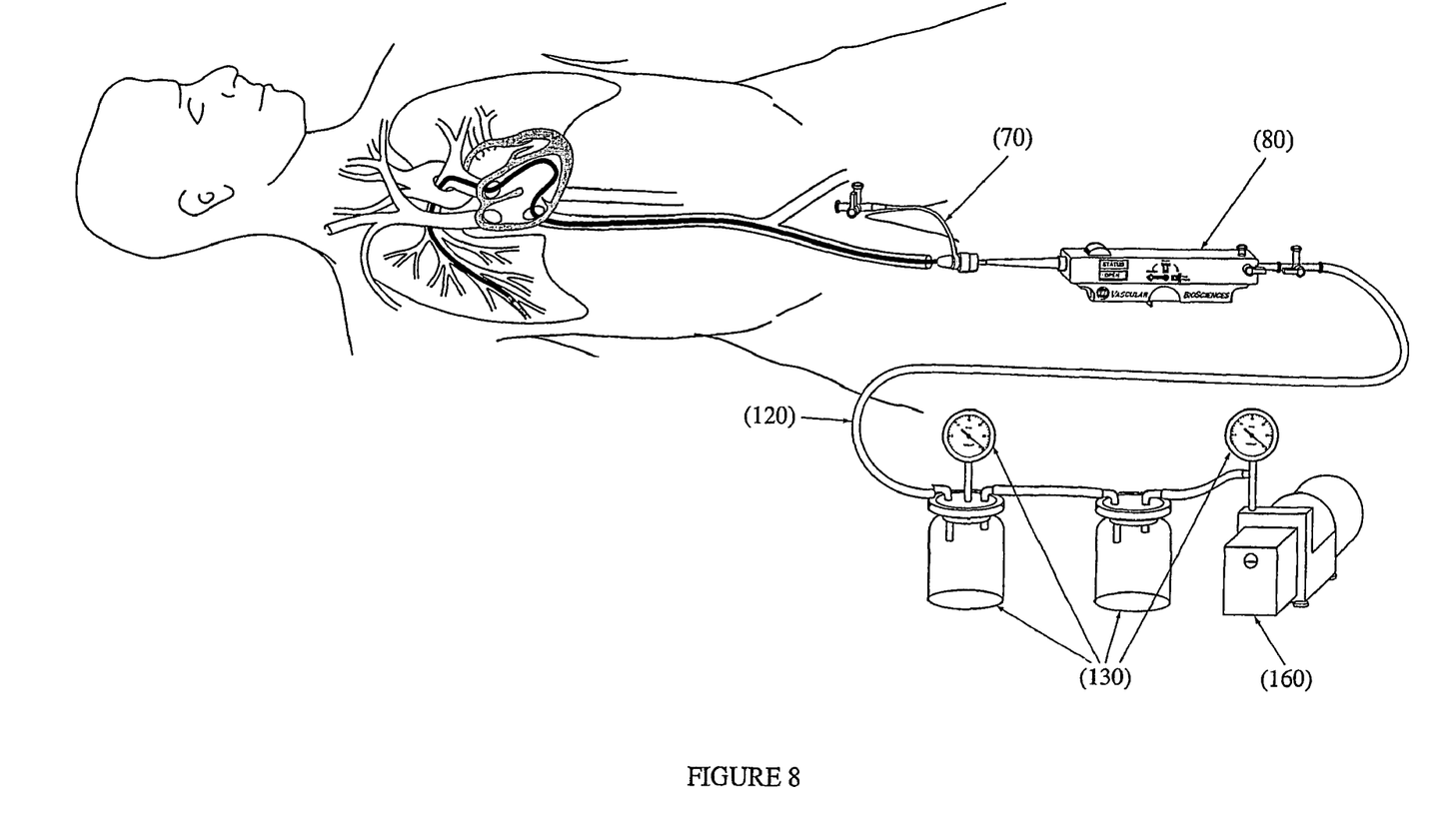
FIG. 8 shows a perspective view of a person in which the catheterization procedure is performed.

The fifth packaging part (280), shown in FIG. 7 contains parts such as the vacuum pump and the vacuum gauges and canisters which can be used several times. Normally, only the first to the fourth packaging part will be present in a standard kit. For new users or as a replacement, the fifth packaging part (280) can be supplied with the other packaging parts (240-270), or by itself.

For example, when the intended purpose of the catheterization procedure is to obtain a biopsy sample for diagnostic purposes to diagnose, for instance, organ transplant rejection or pulmonary vascular disease, the specimen containers can contain formalin, a cryo-preservative solution, a saline solution or other well known ingredients depending upon the diagnostic tests to be performed. When the catheterization procedure is to obtain a biopsy with which to culture cells, autologous vascular grafts, or perform ex-vivo gene therapy, the specimen container may contain a saline solution, a cell culture solution, such as lactated Ringer's solution, or any other solution appropriate to the application.

Upon flushing the endoarterial biopsy catheter with sterile saline solution, the catheter is inspected, and if undamaged, can be reintroduced into the patient to take additional biopsy specimens as desired. Any flushing may be performed using, inter alia, syringes, such as 20 cc syringes, which can be included as components of the present kit.

The kit of the present invention can include an endoarterial biopsy catheter and one or more of the following supplies in a package; a) percutaneous Access needle; b) short introducer sheath with dilator & guidewire; c) floppy guidewire; d) endhole catheter with inflation syringe; e) stiff guidewire; f) flushing syringes; g) long introducer sheath with dilator;

h) needle for specimen removal; i) biopsy cassettes; j) specimen containers; k) connective tubing; l) vacuum gauges & canisters; and, m) vacuum pump.

The skilled artisan will appreciate the need for other accessories which may be useful for performing a catheterization using an endoarterial biopsy catheter. The present invention is intended to include all such additional instruments and equipment to conform a kit to the individual requirements of any particular endoarterial biopsy catheterization procedure. Similarly, the individual components of the kit may be mixed and matched, and the scope of the present invention is intended to include all such permutations and combinations of kit components.

The present invention contemplates a number of catheter kits including a complete endoarterial biopsy kit containing each of the individual components enumerated above. An essential endoarterial biopsy kit would include just a packaged endoarterial biopsy catheter for use by health-care facilities already having in stock the other necessary components to perform a desired procedure. A disposable kit can include all of the previously enumerated components a) through l), excluding the vacuum pump.

The individual components of the kit may be contained in packaging well known to the artisan in the packaging arts. The packaging for the kit of the present invention may be made of one or more of polymers, metals and or fiber materials according to methods known in the art. A vacuum formed polymer tray having recesses containing the kit components and sealed wand placed within a gas permeable TYVEK pouch. U.S. Pat. No. 6,090,076, issued May 23, 2000; U.S. Pat. No. 6,068,121, issued Jul. 18, 2000; and, U.S. Pat. No. 6,065,597, issued May 30, 2000, are herein incorporated by reference in their entirety to provide support for the various modes of the present invention.

All patents and patent applications herein mentioned are specifically incorporated by reference in their entirety, as though fully reproduced.

While the present invention has been described regarding specific embodiments thereof, the artisan of ordinary skill in the art will appreciate that the present invention is capable of further modification. This application is intended to encompass any variations, uses or adaptations of the present invention including those within known and customary practice, within the art to which the invention pertains and as may be applied to the essential features herein before set forth as follows in the scope of the claims. The skilled artisan will appreciate that the present invention can be practiced within a wide range of equivalent components and packaging systems, without departing from the spirit and scope of the invention without undue experimentation.

The invention claimed is:

1. A method of providing a kit for obtaining an endoarterial biopsy sample from a patient, comprising the steps of:

enclosing one or more kit components in a packaging and arranging the one or more kit components in a phased order associated with phases of an endoarterial biopsy sampling procedure, wherein the one or more kit components comprise (a) an endoarterial biopsy catheter, the endoarterial biopsy catheter comprising a distal tip sized for accessing an artery and a means for removing the endoarterial biopsy sample from the artery;

(b) a number of separate packaging parts, the number of separate packaging parts comprising a first packaging part comprising at least one percutaneous accessing component, a second packaging part comprising at least one vasculature accessing component and at least one component selected from the group consisting of specimen containers, biopsy cassettes, needles, vacuum pumps, vacuum gauges and canisters; and (c) returned mail materials to transfer the endoarterial biopsy sample to a remote location.

2. The method of claim 1, wherein the number of separate packaging parts further comprises:

a percutaneous access needle, an introducer sheath with a dilator and a guidewire within the first packaging part; and components for use in accessing a desired area of a vasculature and to provide a sterile connection to a vacuum pump, comprising connective tubing to said vacuum pump, a floppy guidewire, an endhole catheter and a stiff guidewire within the second packaging part.

3. The method of claim 1 wherein the number of separate packaging parts further comprise one or more components selected from the group consisting of a(n): a) percutaneous access needle; b) short introducer sheath with dilator and guidewire; c) floppy guidewire; d) endhole catheter with inflation syringe; e) stiff guidewire; f) flushing syringe(s); g) long introducer sheath with dilator; h) biopsy specimen removal tool; i) biopsy cassette(s); j) specimen container(s); k) connective tubing; l) vacuum gauge(s) and canister(s); and m) vacuum pump.

4. The method of claim 1 wherein the one or more kit components are packed in a vacuum formed tray.

5. The method of claim 4 wherein the kit is enclosed within a gas permeable polymer material.

6. The method of claim 1 wherein the kit is gas sterilized.

7. The method of claim 5 wherein the gas permeable membrane is a synthetic material made of high-density polyethylene fibers capable of allowing water vapor to pass through the membrane.

8. The method of claim 1, wherein the endoarterial biopsy catheter is intended for obtaining the endoarterial biopsy sample of vascular tissue for monitoring indications selected from the group consisting of: organ transplant rejection, pulmonary hypertension, and pulmonary vascular disease by evaluating the endoarterial biopsy sample in a diagnostic laboratory.

9. The method of claim 1, wherein the endoarterial biopsy catheter is intended for obtaining the endoarterial biopsy sample of a vascular tissue for a use selected from the group consisting of ex-vivo gene therapy, making autologous vascular grafts and culturing cells.

* * * * *